(12) United States Patent
Schwartz (10) Patent No.: US 8,178,306 B2
(45) Date of Patent: May 15, 2012

(54) SYSTEMS AND METHODS OF REMOVING AND MANAGING HEAVY METALS

(76) Inventor: Anne Schwartz, Tualatin, OR (US)

( * ) Notice: Subject to any disclaimer, the term of this patent is extended or adjusted under 35 U.S.C. 154(b) by 930 days.

(21) Appl. No.: 12/134,955

(22) Filed: Jun. 6, 2008

(65) Prior Publication Data

US 2009/0075861 A1    Mar. 19, 2009

Related U.S. Application Data

(60) Provisional application No. 60/933,640, filed on Jun. 7, 2007.

(51) Int. Cl.
*C12Q 1/00* (2006.01)
*C07K 14/00* (2006.01)
(52) U.S. Cl. .......................... 435/7.1; 514/2
(58) Field of Classification Search .................. None
See application file for complete search history.

(56) References Cited

U.S. PATENT DOCUMENTS 3,969,244 A    7/1976   Kobayashi
6,322,963 B1   11/2001  Bauer

OTHER PUBLICATIONS

Chailapakul et al., "Fast and simultaneous detection of heavy metals using a simple and reliable microchip-electrochemistry route: An alternative approach to food analysis", Talanta 74: 683-689 (2008; Available Jul. 1, 2007 online).*
Chapman et al., "Differentially ligand-functionalized microcantilever arrays for metal ion identification and sensing", Anal. Chem. 79: 7062-7068 (2007).*
Nolan and Lippard, "A "Turn-On" Fluorescent Sensor for the Selective Detection of Mercuric Ion in Aqueous Media", JACS 125: 14270-14271 (2003).*

* cited by examiner

*Primary Examiner* — Anand Desai
(74) *Attorney, Agent, or Firm* — Farrell Patent Law PC; Mark Farrell (57) ABSTRACT

Systems and methods remove and manage heavy metals. In one implementation, an exemplary method can be applied to food processing and food consumption to remove heavy metals such as mercury, lead, uranium and cadmium before absorption by a living organism. The exemplary method exposes the food to a heavy-metal binding ligand, such as a concentrated protein or phytic acid, to form a heavy-metal chelate, and then allows the chelate to separate from the food. In another implementation, an exemplary probe possesses innovative molecular layers on its surface to detect and quantify heavy metals by attracting and binding traces of the heavy metals on a ligand layer.

7 Claims, 9 Drawing Sheets

SYSTEMS AND METHODS OF REMOVING AND MANAGING HEAVY METALS

RELATED APPLICATIONS

This patent application claims priority to U.S. Provisional Patent Application No. 60/933,640 to Schwartz, filed Jun. 7, 2007, and entitled, "Method of Removing and Managing Heavy Metals," which is incorporated herein by reference.

BACKGROUND

Some metals, such as iron, cobalt, copper and zinc are beneficial to organisms in very low concentrations. But excess amounts of these metals may be detrimental and eventually toxic to organisms, even when their concentration is still low. Other heavy metals, such as mercury, lead, and cadmium, have no known nutritional benefit to organisms, and bioaccumulations of such heavy metals cause adverse health effects.

Heavy metals, such as mercury and lead for example, cannot be metabolized by the body and if accumulated in the body, cause toxic effects by interfering with physiological functions. Yet heavy metals are found everywhere in the environment because they are naturally part of the earth's crust. Moreover, metallic elements, such as cadmium, chromium, copper, lead, mercury, nickel, and zinc are used to manufacture products and are present in some industrial, municipal, and urban runoff as they are used in coatings, paints, lacquers for packaging, toys, furniture, etc. They do not break down or decompose and tend to build up in plants, animals, and people. Thus, they enter living organisms via food, drinking water, and air. Further, removal of heavy metals from organisms is conventionally a difficult process.

SUMMARY

Systems and methods remove and manage heavy metals. In one implementation, an exemplary method can be applied to food processing and food consumption to remove heavy metals such as mercury, lead, uranium and cadmium before absorption by a living organism. The exemplary method exposes the food to a heavy-metal binding ligand, such as a concentrated protein or phytic acid, to form a heavy-metal chelate, and then allows the chelate to separate from the food. In another implementation, an exemplary probe possesses innovative molecular layers on its surface to detect and quantify heavy metals by attracting and binding traces of the heavy metals on a ligand layer.

This summary section is not intended to give a full description of the systems and methods for removing and managing heavy metals, or to provide a list of features and elements. A detailed description of example embodiments follows.

DETAILED DESCRIPTION

Overview

This disclosure describes systems and methods for removing and managing heavy metals. As used herein, the term "heavy metal" refers to a member of the dense, higher atomic weight elements that have metallic properties at room temperature. "Heavy metals" include at least cadmium, chromium, copper, lead, manganese, mercury, nickel, zinc, barium, selenium, and silver, which tend to be toxic in low concentrations and tend to accumulate in the food chain. For purposes of the innovative techniques to be described below, "heavy metals" may also include iron, aluminum, tin, cobalt, gallium, lithium, arsenic, beryllium, vanadium, and even other metals and metalloids. The heavy metal mercury is selected as a representative example for describing the innovative removal and management techniques to be described below. The subject matter described, however, is applicable to many metals.

In one implementation, an exemplary method prevents the absorption of heavy metals by bonding a substance to heavy metal atoms. The resulting bonded substance has properties which allow the bonded heavy metal atoms to be removed, passed, or managed, depending on circumstance. The ligating substance may be a concentrated form of a protein, such as a legume protein, a pulse legume protein, a vegetable protein, a grain protein, etc. Other ligands are also described below. In one implementation, a particular ligand can be selected to target specific metals, such as mercury, or a select group of metals and their ions, such as mercury, lead, uranium, and cadmium.

In various implementations, the exemplary systems and methods utilize the process of chelation for detecting, removing, and managing heavy metals. For example, an exemplary probe assembly to be described below uses innovative molecular layers to attract and bind heavy metals, for their detection and quantification.

In another implementation, a food processing method uses a concentrated protein ligand, a phytic acid ligand, etc., to detoxify fish food from heavy metals, e.g., fish food for fish raised in aquaculture for commercial production and ultimately for human consumption. The exemplary food processing method can also be applied to pet food, such as cat food, dog food, bird food, and food directed toward wildlife rescue, e.g., when a wildlife population is in danger from high levels of heavy metal or other pollutants.

The exemplary food processing method may also be directed to human food processing and food ingestion. For example, the exemplary method may produce a coating, sauce, or marinade to be eaten with fish or other food, that arrests absorption of mercury and other toxic species in the digestive tract.

Certain exemplary ligands may be leveraged in processed foods to scavenge for mercury and other undesirable metals to prevent these from being absorbed in the body. Further, an ingestible form of exemplary ligands may be taken regularly in a diet to aid the body in ridding itself of heavy metals.

As used herein, chelation is a reversible process of bonding a ligand to a heavy metal ion. Ligand, as used herein, means a molecule, or a molecular group, that binds to another chemical entity to form a complex. The resulting complex is referred to herein as chelate. For example, an exemplary method may form a chelate from the heavy metal mercury and the ligand. One example ligand is phytic acid, which has favorable characteristics that include availability and non-toxicity to humans and the environment. Other common names and chemical nomenclature of phytic acid include inositol hexakisphosphate, IP6, and "-phytate" (when in salt form). Phytic acid can be found within nuts, grains, seeds and is commercially available. Besides phytic acid, other ligands may be used in exemplary techniques including, EDTA (Ethylene-Diamine-Tetra-Acetic-Acid), BAL, DMSA (Dimercaptosuccinic acid), DMPS, CDTA, DTPA (Diethylene triamine pentaacetic acid), DPA, TETA (triethylenetetramine), NAC, TIRON, FRO, TRIEN, organic acids, and bacterial metalloregulatory protein (MerR).

The binding of phytic acid to mercury can be optimized for a given removal or management method. In general, for removal and management of heavy metals, a phytic solution is created by placing phytic acid in solution with a fluid, such as water or other solvent. Phytic acid is slightly soluble in water. The solution is placed in contact with surfaces contaminated with the heavy metal or in contact with food that contains undesirable heavy metal. The resulting chelate solution can be moved to a location at which the chelate can be removed from the solution and safely disposed of. The chelate can be filtered out of the solution or sometimes removed via a magnetic process. It is also possible to break the bond between the mercury and the phytic acid via a heating process. This allows the mercury to be re-used for desirable purposes.

Phytic acid has a strong binding coefficient for mercury. When present with mercury and other heavy metals, the phytic acid molecules have a preference for bonding with the mercury atoms over other heavy metal atoms. Therefore, in order to keep the phytic acid from removing desirable metals, for example, calcium or metals of other minerals beneficial to the body (such as zinc, manganese, copper, molybdenum, magnesium and iron), in one implementation just enough phytic acid is placed in solution to bond to an anticipated amount of mercury (e.g., a one-to-one ratio). That is, the concentration of phytic acid in the solution is selected in a stoichiometric ratio to the anticipated amount of mercury.

The above-described general process will now be further described for specific processes.

Food Processing Embodiment

Fish and shellfish are known to contain high levels of mercury due to the accumulative process of biomagnification. Although the exemplary method is described in relation to processing fish and shellfish, the exemplary method is also applicable to processing other animal products that may contain undesirable levels of mercury or other heavy metals.

Figure 1:
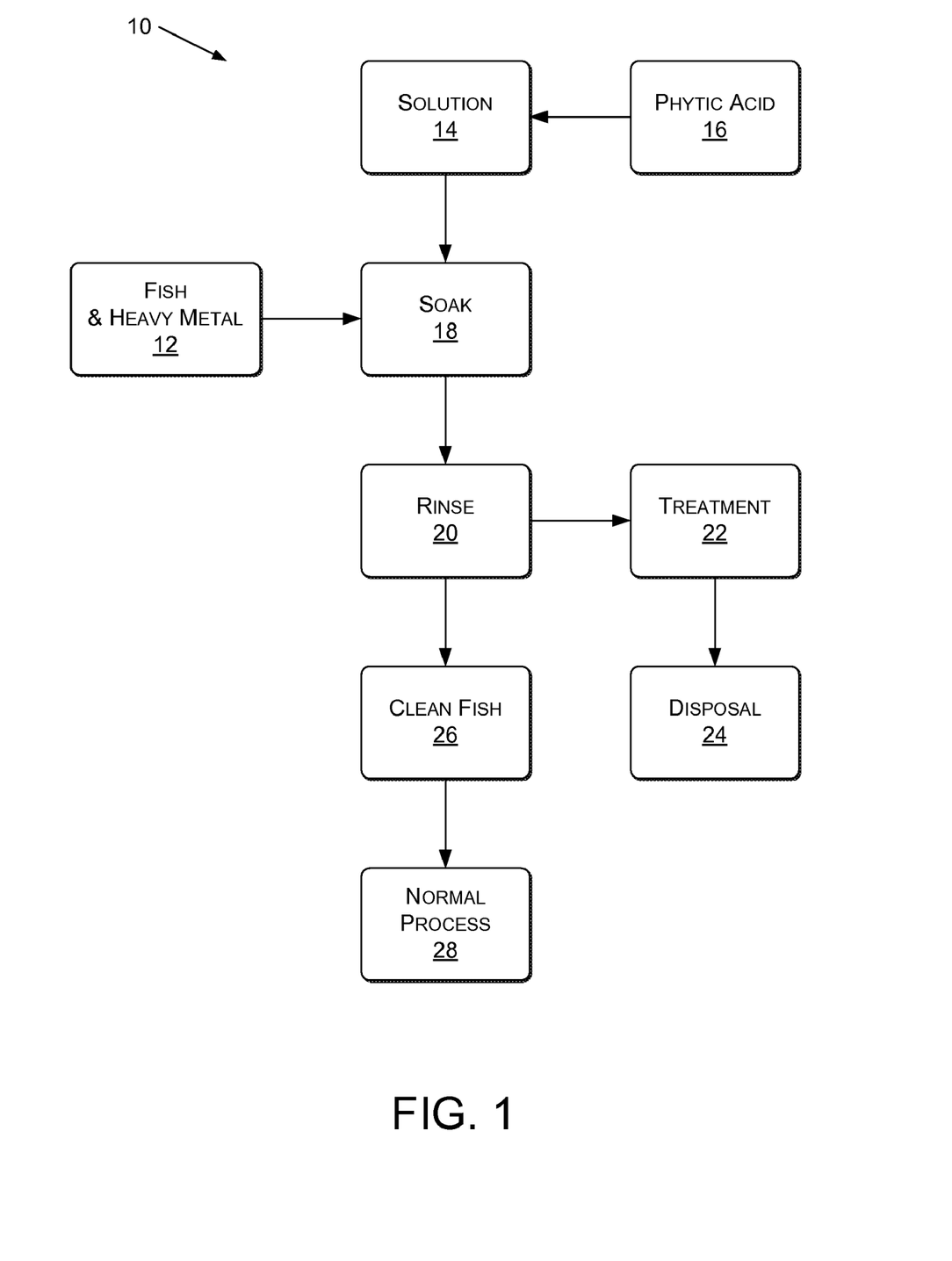
FIG. 1 is a flow diagram of an exemplary process for removing heavy metals from fish.

FIG. 1 shows an exemplary fish processing method 10, i.e., for fish that contain trace amounts of toxic heavy metals, such as mercury ("contaminated fish" 12). A solution 14 contains water and a selected amount of phytic acid 16. During the soaking process 18, phytic acid 16 bonds with mercury in the contaminated fish 12. Optionally, to place the phytic acid 16 deep into the tissue of the contaminated fish 12, it may be desirable to create a vacuum within a container used for the soak 18 prior to introducing the phytic acid solution 14, i.e., to perform the soaking 18 under vacuum. As the vacuum is released, the phytic acid solution 14 may more readily penetrate and permeate the entire tissue of the contaminated fish 12. After a sufficient amount of time has been allowed for phytic acid 16 to permeate the entire fish bulk and bond to the mercury within the contaminated fish 12, for example, from a few seconds to many minutes depending on the granularity of the fish, the contaminated fish 12 is put through a rinse 20, such as water. The resulting water solution containing both the phytic acid solution 14 and the chelate formed by the phytic acid 16 and the mercury of the contaminated fish 12 can then be subjected to a separation treatment 22. Treatment 22 removes the chelate, which can then be disposed 24. Upon rinsing 20, the contaminated fish 12 is transformed into clean fish 26, meaning that the mercury or other heavy metal has been substantially reduced or removed. The clean fish 26 can then be put through its conventional processing 28, which may include further treatments and rinses. In a variation, some steps of the conventional processing 28 may also be incorporated into the exemplary fish processing method 10.

In another implementation, an exemplary ligand such as a concentrated legume protein, a concentrated pulse legume protein (e.g., derived from yellow split peas), a concentrated vegetable protein, or a concentrated grain protein, etc., is used as in the technique just described to detoxify fish food from heavy metals, e.g., to purify fish food for fish raised in aquaculture for commercial production and human consumption. The exemplary food processing method can also be applied to pet food, such as cat food, dog food, bird food, and food directed toward wildlife rescue, e.g., when a wildlife population is in danger from high levels of heavy metal or other pollutants.

The exemplary food processing method may also be directed to human food processing and food ingestion. For example, the exemplary method may produce a coating, sauce, or marinade to be eaten with fish or other food, that arrests absorption of mercury and other toxic species in the digestive tract.

Certain exemplary ligands may be leveraged in processed foods to scavenge for mercury and other undesirable metals to prevent these from being absorbed in the body. Further, an ingestible form of exemplary ligands may be taken regularly in a diet to aid the body in ridding itself of heavy metals.

Surface Treatment Embodiment

Figure 2:
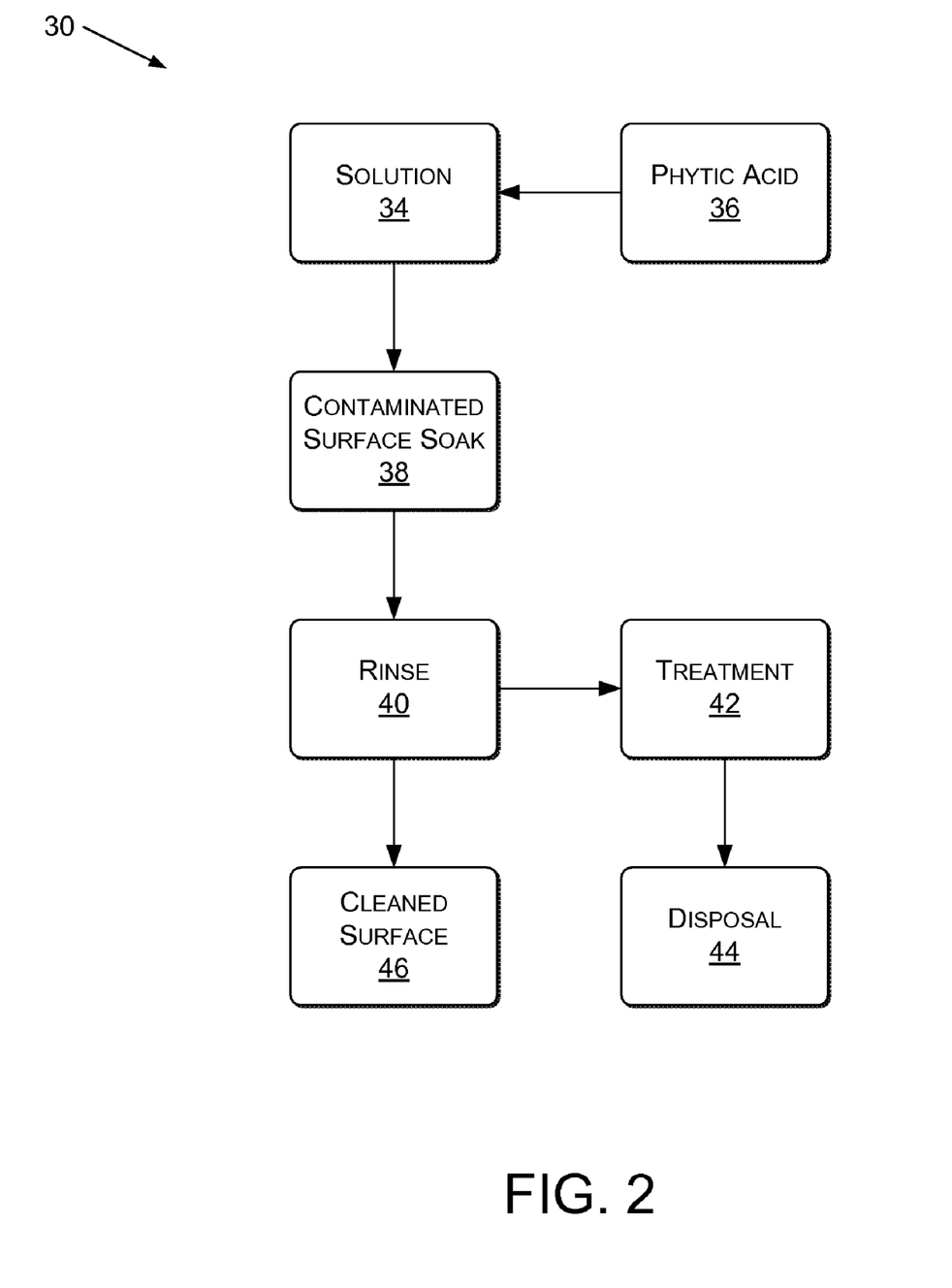
FIG. 2 is a flow diagram of an exemplary process for removing heavy metals from a surface of an object.

Object surfaces are susceptible to heavy metal contamination. Such surfaces include soil surfaces, surfaces of vessels in contact with seawater, such as submarines and ships, and food processing equipment. An exemplary surface treatment method 30 is shown in FIG. 2. Similar to the fish processing method 10 described above, an amount of phytic acid 36 is mixed into a solution 34. The resulting solution 34 is then applied to a contaminated surface at which the solution 34 is allowed to soak 38 or is scrubbed into the surface creating a chelate between the phytic acid 36 and the mercury or other heavy metal. The resulting chelated soak can be removed from the surface by rinsing 40. The chelate can then be removed from the rinsed off solution via a separation treatment 42 and then disposed 44. The disposal 44 may include containment, or, separation of the mercury and phytic acid 36 as previously described. The result is a clean surface 46 substantially free of the heavy metal.

In one embodiment, an exemplary surface treatment modality constitutes a skin cream, that may be applied to workers who have contact with pollutants, especially those that contain heavy metals. A mining waste, an exploding bullet, or a nuclear power or warfare event may produce various uranium and other heavy metal derivatives, which can be chelated and rendered harmless or manageable by various exemplary binding agents described herein.

Submarine Water Filtration Embodiment

The exterior surfaces of submarines are known to be collectors of heavy metals such as mercury. Because fresh water is needed onboard the submarine, seawater is often collected into the submarine via a contaminated exterior surface and the seawater processed to remove salts. This submarine water collection and desalination is a well-known and well-understood process. A problem with bringing seawater through the hull of the submarine is that the heavy metal contaminated surface of the submarine acts as a concentrator for the heavy metals and also contaminates the water to be processed for consumption within.

Figure 3:
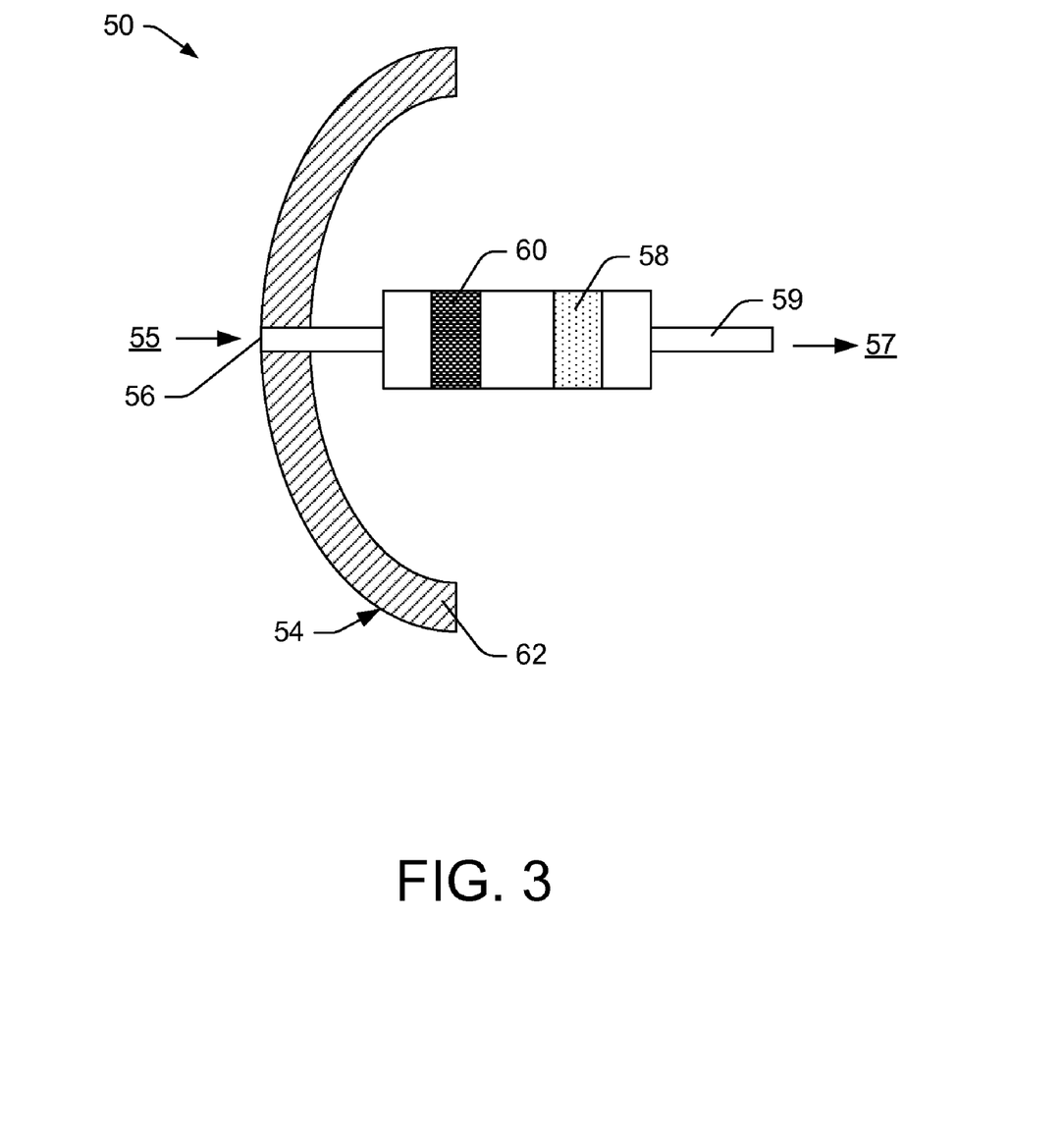
FIG. 3 is section view of a submarine water intake and exemplary heavy-metal filtration system.

FIG. 3 shows an exemplary system for removing mercury and heavy metals from the inlet water of a submarine. Exemplary submarine filtration assembly 50 is comprised of a submarine hull 52, which has an outer surface 54. Outer surface 54 contains an amount of mercury that also combines with seawater being collected to produce contaminated seawater 55. The contaminated seawater 55 enters the submarine through an inlet 56.

In one implementation, a chelating filter 60 intervenes to bond phytic acid to the mercury or other heavy metal contained within the contaminated seawater 55. Chelating filter 60 may be a fabric-like material. An outlet 59 provides a supply of non-contaminated seawater 57 with the mercury or other heavy metal substantially reduced. The outlet 59 may pass the decontaminated water to conventional desalination methods and equipment. Also shown in FIG. 3 is an optional carbon filter 58. The carbon filter 58 may absorb additional trace amounts of mercury. The two stage process may produce a cost-effective and efficient overall filtration system for treating seawater before desalination. Chelating filter 60 may be removed and replaced as needed. In one implementation, the chelating filter 60 has phytic acid embedded on the material like fibers or fabric of the filter 60. In another implementation, the chelating filter 60 receives a constant flow of phytic acid solution measured in ratio to the incoming seawater, and the fibers of the chelating filter 60 mix the seawater and the phytic acid solution together to bind the mercury with the phytic acid.

Absorption-Prevention Embodiment

Figure 4:
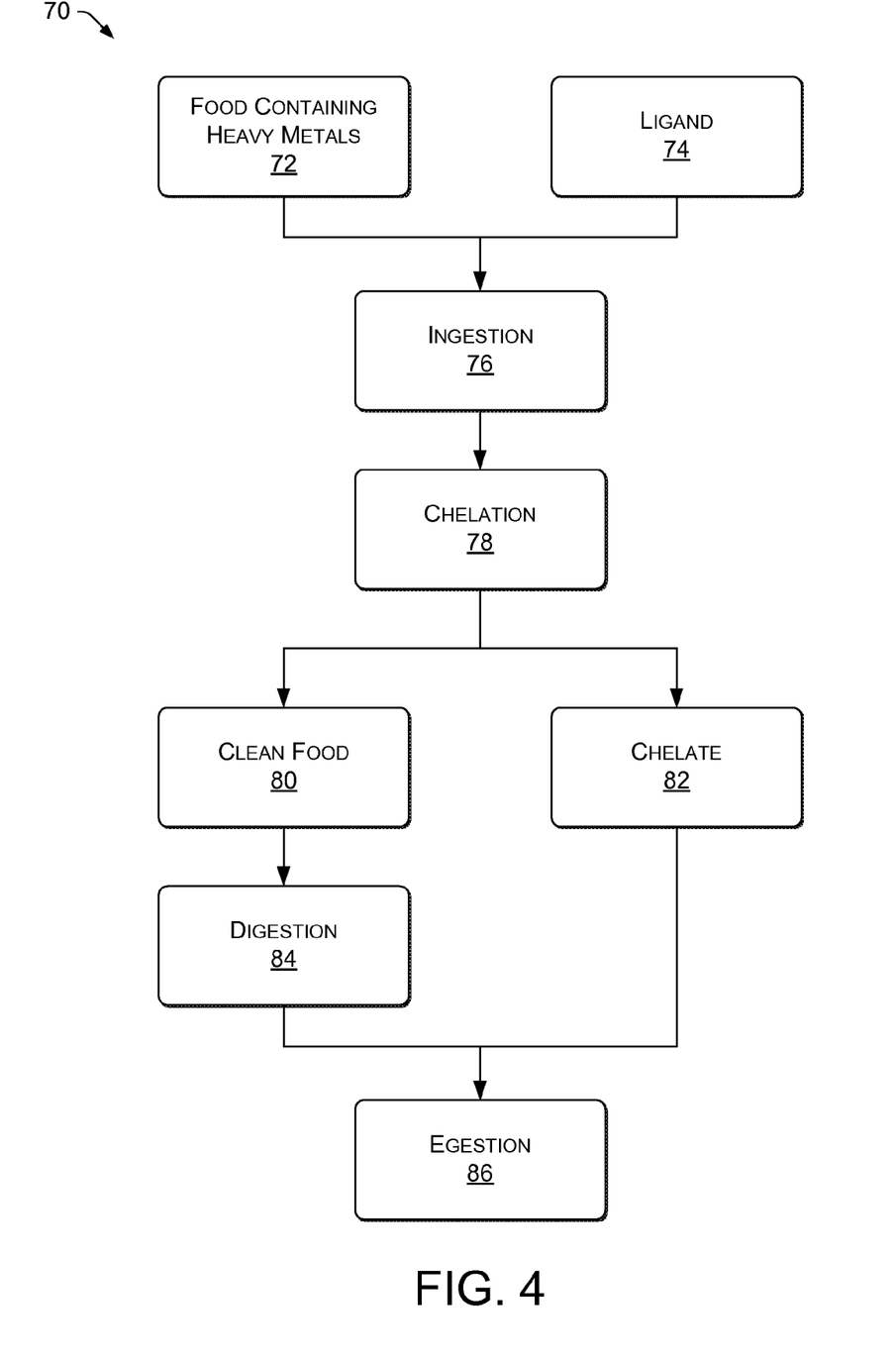
FIG. 4 is a flow diagram of an exemplary heavy-metal absorption prevention method.

FIG. 4 shows an exemplary anti-absorption method 70 for preventing absorption of mercury or other heavy metal by a living organism that has ingested food that has a concentration of heavy metal. Rather than allowing the organism to digest the mercury and then trying to remove the mercury from the tissue of the body, the exemplary anti-absorption method 70 intervenes by chelating the mercury prior to its digestive transfer to the body, thus preventing absorption of the mercury into the bloodstream or intestinal mucosa.

An amount of food 72 that may contain a concentration of the heavy metal ("contaminated food") is consumed with an amount of the ligand 74, or, near the time of consuming the ligand 74. In one implementation, the ligand 74 is phytic acid. The ligand 74 is preferably in an amount suitable for at least substantially bonding to the mercury contained within the food 72. The ligand 74 may be prepared in the form of a marinade or sauce directly applied to the food 72, or may be a separate supplement such as a pill, alternate food source, or the like. Ingestion 76 may provide mixing of the food 72 and ligand 74. When the food 72 and ligand 74 are mixed, then chelation 78 causes the mercury or other heavy metal in the food 72 to bond to the ligand 74, thereby forming a chelate 82. The chelate 82 causes food 72 containing some mercury to become a clean food 80, substantially free of the mercury. The clean food 80 proceeds to normal digestion 84, while the chelate 82 proceeds to safe egestion 86 from the body. Thus, the mercury contained within food 72 is passed through the living organism without digestion 84. Testing has shown that chelation between mercury and phytic acid can occur at a wide range of pH levels, including acidic levels commonly found in the stomach.

Various workers and soldiers are commonly exposed to heavy metals in their occupational environment. As a dietary component, an exemplary ligand or combination of ligands, such as a concentrated legume protein, a concentrated pulse legume protein, phytic acid, etc., can be taken as part of a regular diet to help the body rid itself of heavy metals and other pollutants. Typically, heavy metal derivatives, e.g., from artillery fire enters the body through the lungs or digestive tract, and are slowly broken down or bound by the liver to be passed in elimination via the biliary tract. However, the various chemical species can be reabsorbed along this physiological route. Thus, the exemplary ligands prevent the harmful metals from being reabsorbed before they can be eliminated.

Mercury/Heavy-Metal Detection Embodiment

Figure 5:
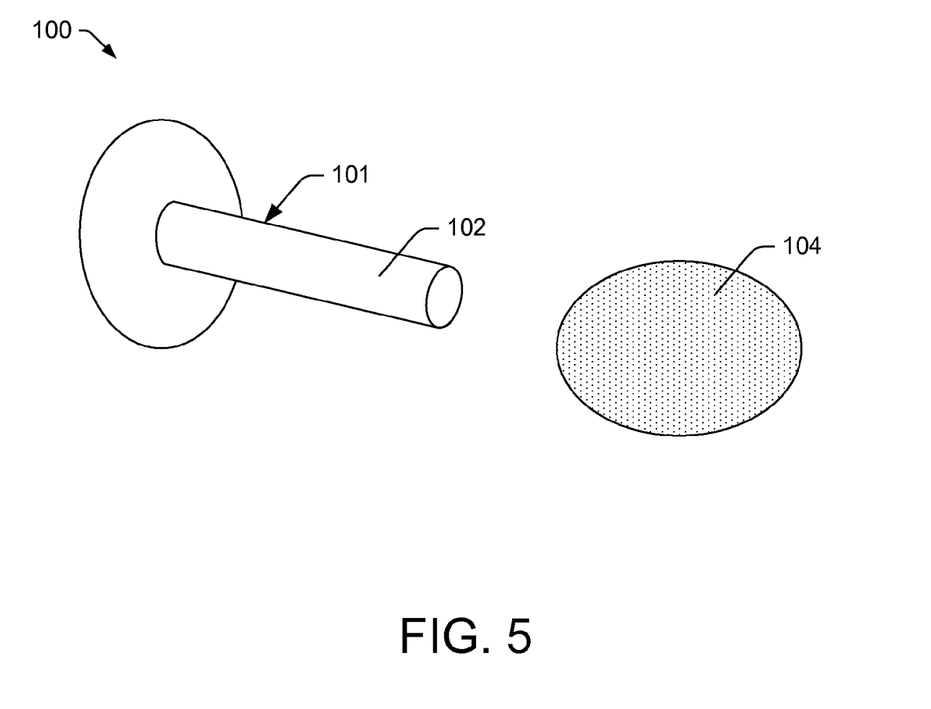
FIG. 5 is a perspective view of an exemplary measuring probe for detecting and quantifying heavy metals.

FIG. 5 shows a device for detecting and measuring the heavy metal content of a substance. In FIG. 5, a probe assembly 100 has a structural member 101 that possesses a ligand surface 102. The probe assembly 100 is inserted or placed in direct contact with a contaminated object 104, so that the ligand surface 102 can bond to some of the heavy metal contained on or within the object 104. Upon removing the probe assembly 100 from the contaminated object 104, some of the heavy metal is removed with the ligand surface 102.

Figure 6:
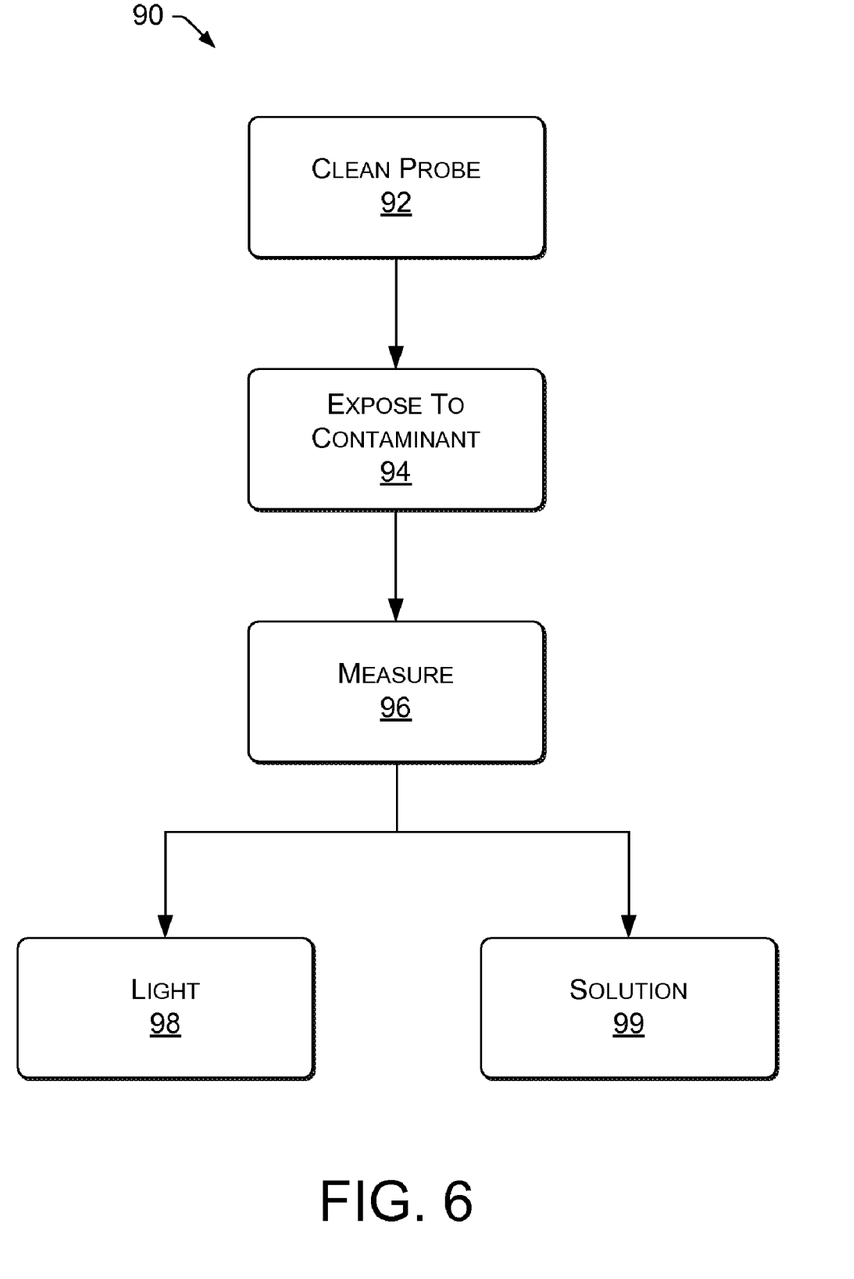
FIG. 6 is a flow diagram of an exemplary method of measuring heavy metals.

FIG. 6 shows the subsequent heavy-metal measurement process associated with the probe assembly of FIG. 5. At block 92, the probe assembly 100 of FIG. 5 is initialized by exposing the ligand surface 102 to an acidic solution that refreshes the ligand surface for a new measurement test. Phytic acid can be used in various forms on the ligand surface 102 allowing the sensor to be reused, since the sampled metals are released when the pH is lowered. The innovative probe assembly 100 is used for metal binding and release, and can also be used with other organic, environmental, and biological substances.

At block 94, the probe assembly is exposed to a contaminant, i.e., a contaminated object 104 that may have heavy metals contained on its surface or within its interior. At block 96, the amount, level, or concentration of heavy metals in the sample that binds to the ligand surface 102 is measured, e.g., via such means as spectroscopic or spectrophotometric measurement of light reflection and quality of color 98 or through chemical analysis, such as qualitative and quantitative analysis of a test solution 99 derived from the ligand surface 102.

In one implementation, the sampled amount of heavy metal on the ligand surface 102 can be compared against known chelation rates between the heavy metal and the chosen ligand to derive an estimated amount of heavy metal actually in or on the contaminated object 104. In one implementation, the probe assembly 100 uses a phytic acid ligand surface 102 for measuring mercury content within fish.

A Nano-Based Heavy-Metal Sensor

In one implementation, a nano-based sensor used for environmental tests, medical tests, and diagnostics and can be further modified to include a capability to detect and measure heavy metals, colliforms, E-coli, dissolved oxygen, nitrate and nitrites, poisons, e.g., arsenic, pesticides and fertilizers. A conventional nano-based sensor can be modified with additional molecules to construct an exemplary innovative nano sensor. For example, the conventional nano-based sensor may be similar to that described in U.S. Patent Application Publication No. 2007/0256941 to Prasad et al., entitled, "Nano-porous membrane based sensors," filed Dec. 4, 2006, and incorporated herein by reference.

Example environmental sensor applications include point-of-use (e.g., handheld) and remote sensing (e.g., ongoing sensing of the environment). The particular analytes to be detected by the exemplary sensor can include, for example, heavy metals, (e.g., many known forms of mercury, lead, cadmium, uranium, and iron), gases for air quality (including petroleum product vapors, methane, sulfur dioxide, carbon monoxide, oxygen, particulates, and nitrous oxide), water quality contaminants (PCBs, poisons such as arsenic, dioxin, bacteria, mold, algae, and dissolved oxygen), structural infestations (organically, mold and bacteria; inorganically, carbon monoxide). The exemplary sensor can also implement diagnostic applications that directly relate to the effect that these environmental contaminants have on the health of humans and animals, including sensing HIV viral RNA, Tuberculosis bacterial DNA; Malaria and other parasite DNAs, anitibodies, and oxidative stress markers associated with the above etiologies.

In one implementation, an innovative construction technique adds a molecule to the surface of the exemplary sensor that acts as an intermediate to bind substances that would not otherwise bind to conventional sensor surfaces. This allows more types of substances to bind than could bind using the conventional surface chemistry of conventional nano wells on the probes. This allows various forms of phytic acid to chelate metals and proteins that also complex with metals, environmental substances, and biological substances.

In one implementation, the exemplary sensor immobilizes a solid-phase chelator-binding substance that binds to the nano wells of the exemplary sensor (or other assay system). For example, polyethyleneimine polycation can be applied to a conventional sensor surface to serve as a way to bind a concentrated protein, such as a pulse legume protein, phytic acid, EDTA, etc., to the exemplary sensor surface, which can then chelate metals or other select pollutants. Other intermediates may also be used, such as metaloenzymes, carboxylases, metals, salts, and nucleic substances for intermediate binding of specific targets.

Figure 7:
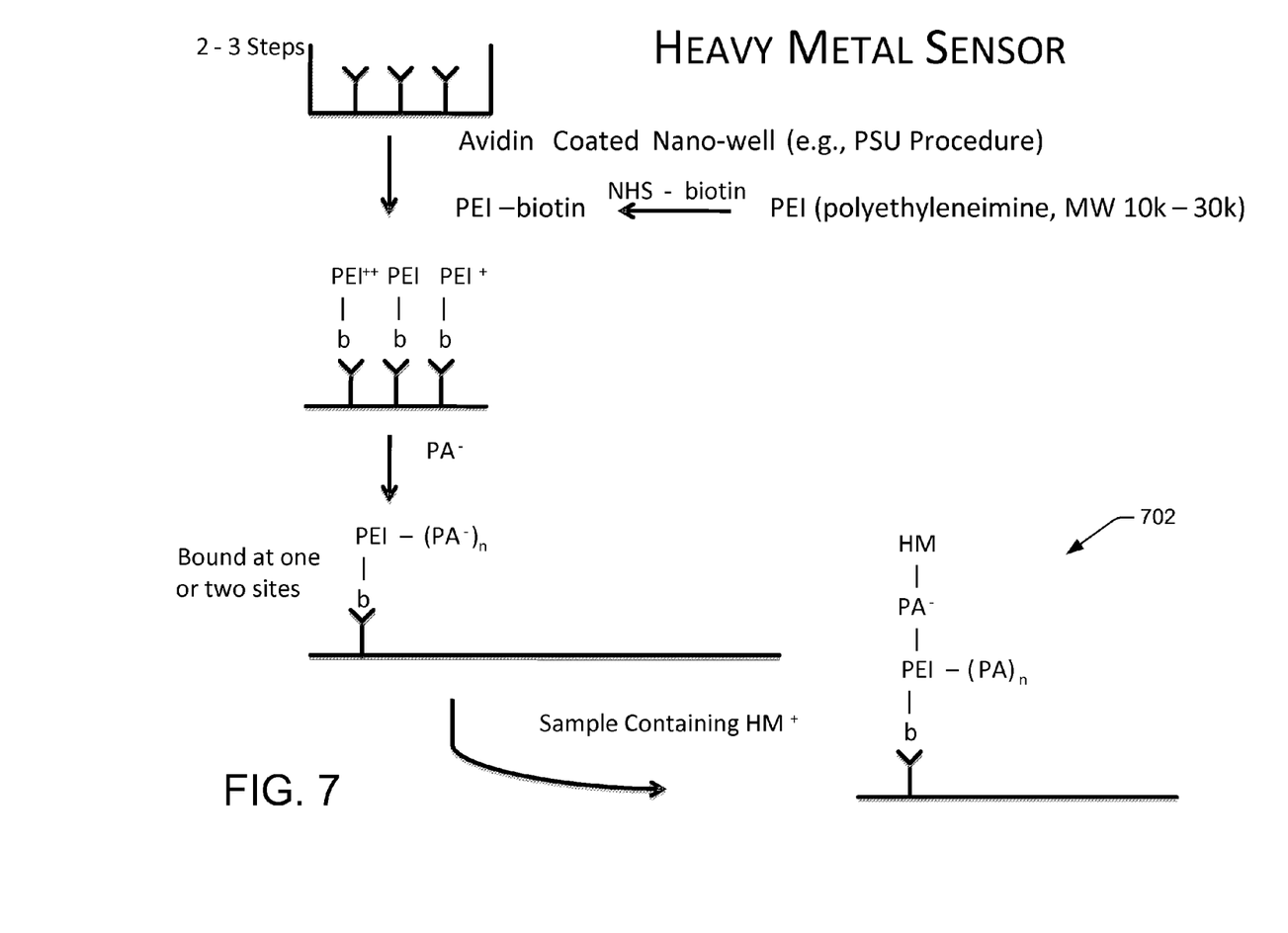
FIG. 7 is a diagram of an exemplary nano-based sensor for detecting and quantifying heavy metals.

FIG. 7 shows the above-described molecular layers 702, such as polyethyleneimine applied to a nano-porous membrane-based sensor to bind phytic acid, which in turn binds a heavy metal for detection and quantification.

Simultaneously Measuring an Array of Substances in a Single Sample

An exemplary sensor element consists of one or more sensing sites, each of which is sensitized to a different target substance. The system may include a unique impedance measurement block for each sensing site; or, a single impedance measuring block may be connected sequentially to each site. For a sensor element consisting of more than one sensing site, the calibration consists of both the characteristics of each site in response to its target substance and also the cross sensitivities of each site to the target substances of the other sites. This allows a calculation to be performed on the measurement results for the multiple-site sensor that improves its accuracy and its ability to differentiate between multiple target substances in a single sample.

In an example implementation, the exemplary sensor can identify substances in whole blood and/or saliva, such as molds, heavy metals allergens, and parasites.

Either hand-held implementations or remote monitoring implementations are capable of real-time measurement of heavy metals in air and water. The mechanism can be similar for both, e.g., when the analysis for substances in air uses dissolution of the airborne substances in a solution.

Remote Monitoring System

In one implementation, an exemplary sensor system includes 1) a disposable sensor element; 2) an electrical impedance measurement block; 3) a fluid sample delivery system; 4) a system controller; and optionally 5) a remote communications block.

The disposable sensor element has the electrical characteristic that its impedance changes when it is exposed to a sample fluid containing a target substance to which it has been sensitized. The change in impedance is proportional to the concentration of the target substance in the fluid.

Different sensor elements, or sensor elements sensitized to different target substances, have different impedances and relationships of impedance to concentration of the target substance. The characteristics of each sensor configuration are determined by laboratory calibration and then loaded into the system for use with sensor elements of that configuration. In one embodiment, the characteristics and/or calibration information is contained onboard each sensor element and is automatically retrieved by the system controller when the sensor element is attached to the system. In an alternative embodiment, the sensor element contains only information identifying its type. In this case, the characteristics information is held by the system controller. In another alternative implementation, the information is entered by an operator, either at the time of system configuration or at each use.

The electrical impedance measurement block contains the electrical circuitry to connect to the sensor element and to measure its electrical impedance. The impedance measurement block produces an output that is proportional to the impedance of the sensor element.

The output can be continuously monitored as the sensor element is exposed to the sample fluid. In one implementation, this output is in the form of digital data; however, an analog signal, either voltage or current, is also possible. Measurement of the electrical impedance consists of applying an alternating current (AC) signal to the sensor and determining the relative magnitude and phase of the voltage across the sensor and the current flowing through it. Impedance is the total measure of opposition to electric current and is the complex vector sum of resistance and reactance. Determination of parameters can be accomplished either directly by measurement of the voltage and current or indirectly by comparison against a known, reference, impedance. The frequency of the applied AC signal can be varied in order to provide an optimum measurement configuration for sensors with differing values of impedance.

The system controller is comprised of a microprocessor or microcontroller, memory, power supply, etc. The system controller configures the electrical impedance measurement block, operates a fluid sample delivery system, and presents measurement results and status information to the system operator either directly via local display in the case of a hand-held implementation; or, via remote communications for a remote monitoring implementation.

In some implementations, the fluid sample delivery system draws a sample from a fluid to be tested and delivers the sample to the sensor element. The fluid sample delivery system can include filtering to remove particulate contaminants that would interfere with operation of the fluid sample delivery system or with the operation of the sensor element. The fluid sample delivery system includes the ability to flush itself of residue left from previous sampling actions before delivering the new sample to the sensor element.

The optional remote communications block allows the system to operate as a remote monitor. The system is designed to permit the use of remote communications blocks supporting a wide variety of communications systems. These include, but are not limited to, IEEE 802.11 (WiFi), IEEE 802.16 (WiMAX), IEEE 802.15(Zigbee), UMTS 3G Cellular, or GPRS Cellular. Via the remote communications block, a remote operator can configure and control the system, retrieve measurement and status information, and perform diagnostic testing.

Exemplary Experimental Results

In the context of preventing mercury from being absorbed in the digestive tract of a living organism, experiments were conducted and subjected to statistical analysis.

Phytic acid, mercury binding proteins, and/or some food components that contain phytic acid (e.g., filtered or processed food components that are naturally occurring or/and concentrated that contain relatively high levels of phytic acid or/and metal binding proteins or/and amine molecules) when added to food (e.g., in a proportion that ranges from approximately 0.1% to 60% by weight of the food) will inhibit metal absorption by complexing with heavy metals. In birds, fish, animals, mammals, etc., the resulting complex is then eliminated through the colon. Thus, phytic acid can be used as a metal scavenger in processed foods and drinks.

Figure 8:
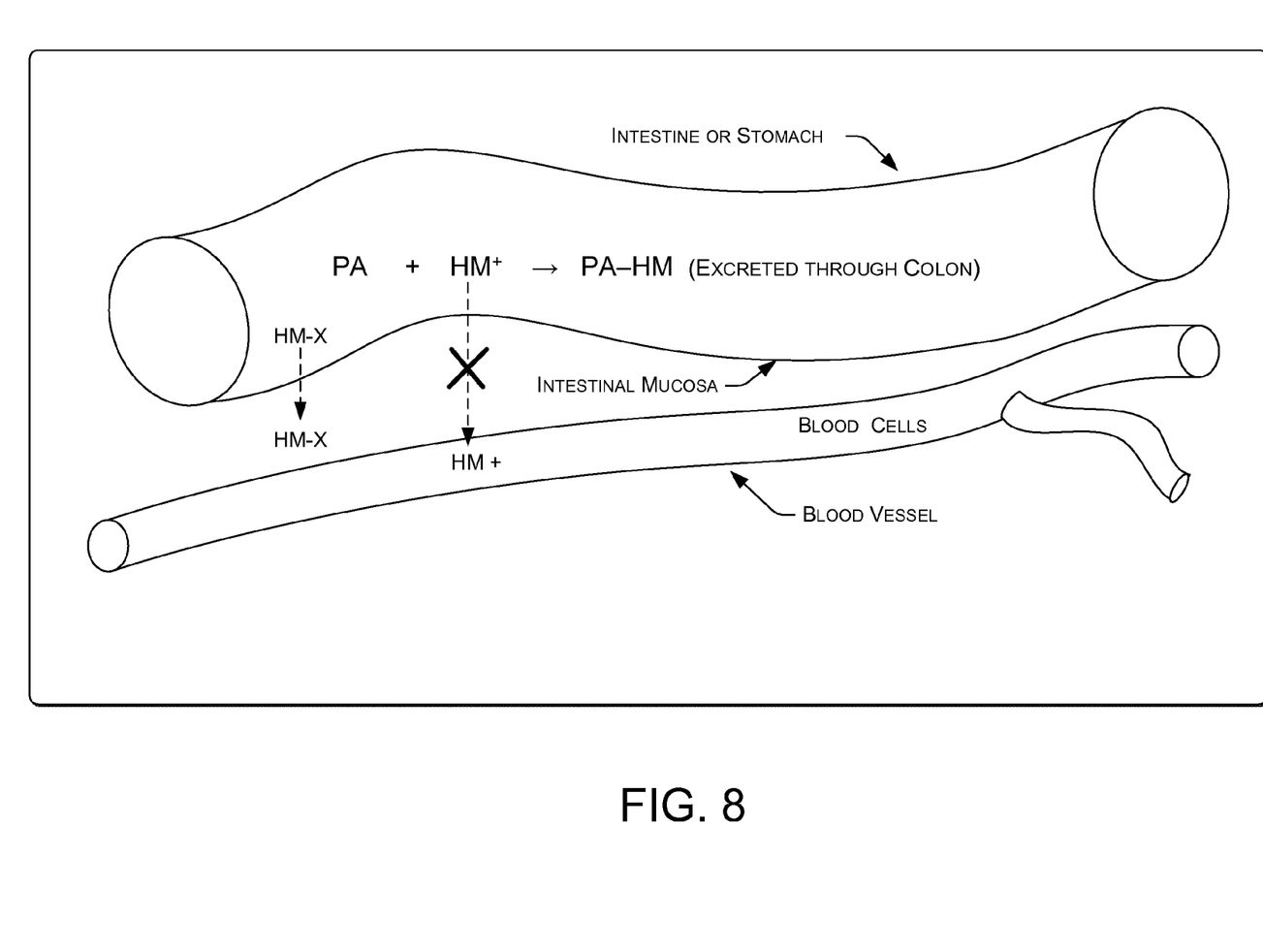
FIG. 8 is a diagram of binding a heavy metal in an intestine of a living organism to prevent absorption of the heavy metal by the organism.

FIG. 8 shows a mechanistic action diagram for an example experiment, in which mercury (Hg) in the stomach or in an intestinal cavity of the digestive system is intercepted by phytic acid (PA), thus preventing the mercury from being absorbed through the lining of the digestive system.

In FIG. 8, the abbreviations mean:
PA=Free or Fiber Complex Phytic Acid
HM=Heavy Metal (i.e. Pb, Hg)
HM-X=Organometallic Compound
And the chemical binding reactions are symbolized by:

$PA^{-6}+HM+^{2}\rightarrow(PA)(HM)^{(1-3)}(\text{Complex})$ $HM\text{-}X+PA\rightarrow(PA)(HM\text{-}X)^{(1-3)}$ To test the hypothesis that phytic acid (e.g., as found in food components high in levels of phytic acid or/and metal binding proteins or/and amine molecules) will complex with heavy metals in food inside a living organism (or externally to the organism) and prevent metals from being absorbed in the organism's digestive tract, the example experiment used 44 Zebra Fish as the test population.

Prior to the study, tests were performed on concentrated (80%) split yellow pea protein, concentrated chick pea protein (40%) and phytic acid to determine if in a salt solution these substrates would bind mercury. The test indicated that substrates would bind mercury so the study was conducted.

Methods:

Following EPA Method 7473, a total of 44 Zebra fish were randomized into four one gallon tanks and fed an experimental or control diet for 6 days. On the seventh day the fish were not fed so that any food being digested would have been absorbed or eliminated. The fish were fed 1.0 gram of food twice a day the first day. On the second day the fish were fed 0.5 grams twice a day. On days 3-6 the fish were fed 0.5 gram once a day. This difference in feed amount occurred as a result of identifying the maximum amount the fish would eat a day.

The control and experimental feed was prepared using:
3 g. Cornstarch
11.2 g. Fish Flakes
9.8 g. Frozen Thawed Brine Shrimp
30 g. Water The corn starch and water were boiled for 2 minutes then mixed with the remaining ingredients. The basic food was divided into four groups. The study groups consisted of: the control (Group C), an experimental group in which phytic acid di-sodium salt was added to the feed at 5% by weight of the fish (Group A), an experimental group in which 15 μg mercuric iodide salt per gram of food was added (Group B), and lastly Group D in which fish were fed the above stated amounts of mercuric iodide salt and phytic acid di-sodium salt.

The analysis was conducted by a contracted company, Northwest Pacific Labs. Samples were stratified by treatment and randomly sampled. A test of atomic absorption was used to determine absorbed mercury, after calibrating the instrument.

Results

Figure 9:
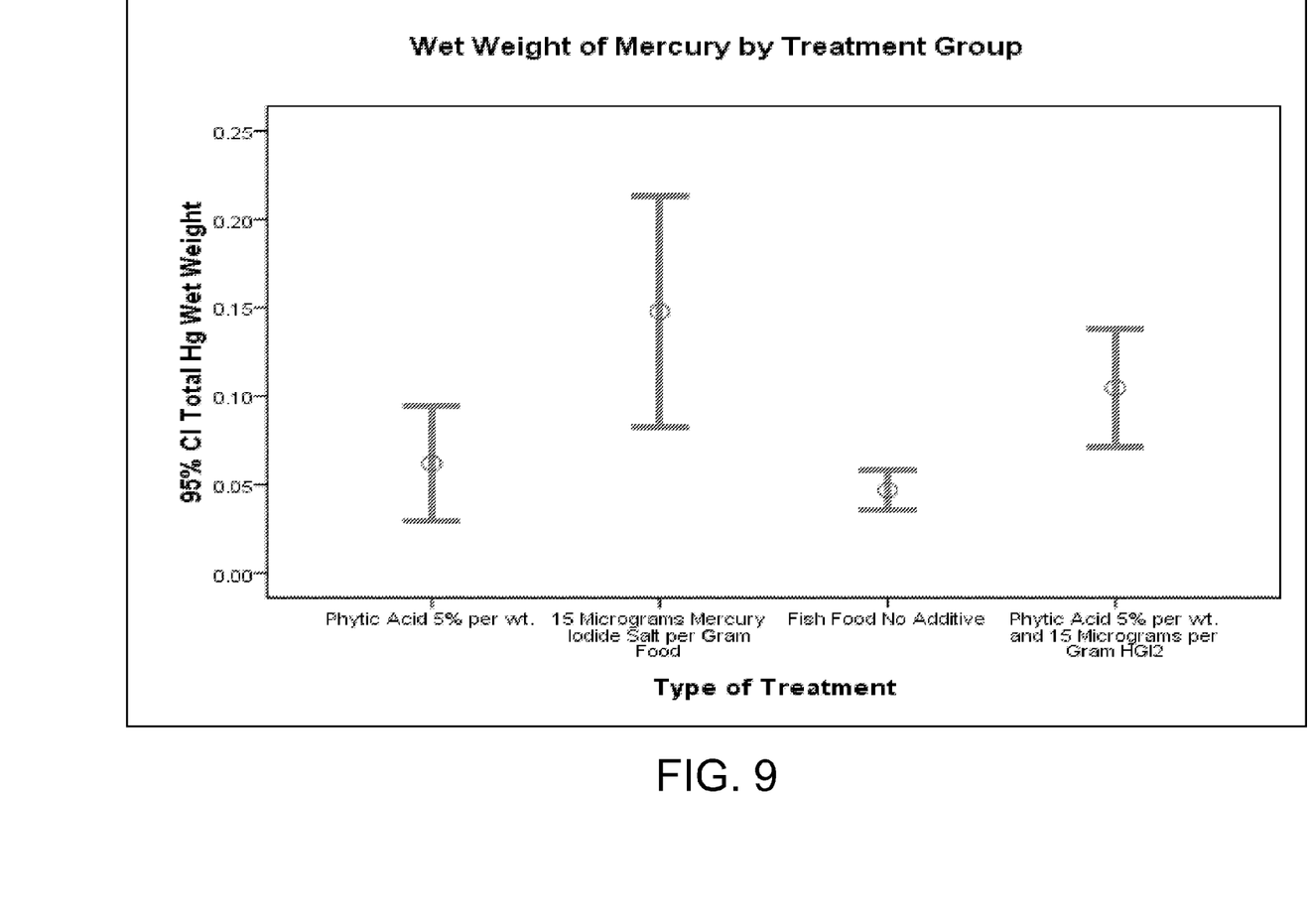
FIG. 9 is a diagram summarizing results of an experiment preventing living organisms from absorbing mercury.

FIG. 9 shows a summary of experimental results between types of treatment groups. A Kruskal Wallis Test was used to determine mean group differences. Results indicate that there was a significant (asymp sig. 0.012) difference between groups for wet mercury weight. The control and phytic acid only (C) group were significantly lower in mercury as seen in Table (1), below.

TABLE 1

Test Results of Mercury Absorption Across Treatment Groups
Total Hg Wet Weight

| Type of Treatment | Mean | N | Std. Deviation |
|---|---|---|---|
| Phytic Acid 5% per wt. | .0621 | 4 | .02054 |
| 15 Micrograms Mercury Iodide Salt per Gram Food | .1478 | 4 | .04118 |
| Fish Food No Additive | .0469 | 4 | .00698 |
| Phytic Acid 5% per wt. And 15 Micrograms per Gram HGI2 | .1047 | 4 | .02100 |
| Total | .0904 | 16 | .04661 |

This result was expected since neither of those groups were given mercury. Although the two experimental groups with mercury were not significantly different from each other, mercury absorption was reduced by 50% in group D that included phytic acid as well as mercury when baselines of mercury were controlled for. It is worth noting that large differences were not expected in this seven day time frame because heavy metals take at least three weeks to build up.

Table (2) shows mercury total weight by type of treatment test statistics:

TABLE 2

Mercury Total Weight by Type
of Treatment Test Statistics[a, b]

|  | Total Hg Wet Weight | Fish Wt. |
|---|---|---|
| Chi-Square | 11.029 | .551 |
| df | 3 | 3 |
| Asymp. Sig. | .012 | .907 |

[a]Kruskal Wallis Test
[b]Grouping Variable: Type of Treatment

As shown in TABLE (3), to determine if the significance between groups B and D was being underestimated, the sample was weighted to prevent errors in estimation due to the small sample size. Results indicate that the phytic acid and mercury group D contain significantly (Sig=0.000) less absorbed mercury than did the mercury-alone group B.

TABLE 3

Mean Comparison of Mercury Wet
Weight Between Groups B and D Test
Statistics[a]

| | Total Hg Wet Weight |
|---|---|
| Mann-Whitney U | 2500.000 |
| Wilcoxon W | 7550.000 |
| Z | −6.157 |
| Asymp. Sig. (2-tailed) | .000 |

[a]Grouping Variable: Type of Treatment

CONCLUSION

Although exemplary systems have been described in language specific to structural features and/or methodological acts, it is to be understood that the subject matter defined in the appended claims is not necessarily limited to the specific features or acts described. Rather, the specific features and acts are disclosed as exemplary forms of implementing the claimed systems, methods, and structures.

The invention claimed is:

1. A system for measuring heavy metals or pollutants, comprising:
   a sensor for detecting a presence of a heavy metal or pollutant on a surface or associated with an object;
   a ligand surface on the sensor for receiving a sample amount of the heavy metal or pollutant from the surface or from the object for measurement;
   wherein the ligand surface binds with atoms or ions of the heavy metal or pollutant in a ratio representative of the heavy metal or pollutant on the surface or in the object;
   wherein the sensor comprises a nano-porous membrane-based sensor and a binding agent is applied to nano wells of the nano-porous membrane-based sensor in order to secure a ligand to the nano wells, the ligand binding the heavy metal or pollutant for measurement by the nano-porous membrane-based sensor; and
   wherein the ligand comprises one of a legume protein, a pulse legume protein, a vegetable protein, a grain protein, EDTA, phytic acid, or a phytic acid derivative.

2. The system of claim 1, further comprising a swab possessing the ligand surface to collect a heavy metal or pollutant sample.

3. The system of claim 1, further comprising an elongated member to support an area of the ligand surface suitable for quantifying the heavy metal or pollutant via analytical processing, including one of chemical, spectroscopic, spectrophotometric, electric, or electronic analytical processing.

4. The system of claim 1, wherein a measured amount of the heavy metal or pollutant is compared against known chelation rates between the heavy metal or pollutant and a selected ligand in the ligand surface to determine an estimated amount of the heavy metal or pollutant on the surface or in the object.

5. The system of claim 1, wherein the sensor includes multiple sensing sites, each sensing site tuned to a different target heavy metal or pollutant.

6. The system of claim 1, wherein a binding of the heavy metal or pollutant to the ligand surface is reversible to enable ongoing real-time measurement of heavy metals or pollutants in an environmental setting including in air and in water.

7. The system of claim 1, further comprising an electrical impedance measurement block;
   a fluid sample delivery system; and
   a system controller;
   wherein the sensor undergoes a change in electrical impedance in proportion to an exposure to a fluid containing a concentration of a targeted heavy metal or pollutant.

* * * * *